United States Patent
Carew et al.

(10) Patent No.: US 6,277,360 B1
(45) Date of Patent: *Aug. 21, 2001

(54) WASHING COMPOSITION

(75) Inventors: Peter Simon Carew, Bebington (GB);
Peter Gallagher, Buxtehude (DE);
Peter Christopher Konidaris,
Bebington (GB); Stanley Lam,
Bangkok (TH); Euan Stuart Reid,
Bebington (GB); Ian Berkeley Walton,
Bangkok (TH)

(73) Assignee: Helene Curtis, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/196,816

(22) Filed: Nov. 20, 1998

(30) Foreign Application Priority Data

Nov. 26, 1997 (GB) .................................................. 9725013

(51) Int. Cl.[7] .............................. A61K 7/06; A61K 9/127; A61K 31/44; A01N 25/00
(52) U.S. Cl. ....................... 424/70.12; 424/405; 424/450; 514/358; 514/938; 516/276
(58) Field of Search .................. 424/70.12, 405, 424/450; 514/358, 938; 510/276, 292

(56) References Cited

U.S. PATENT DOCUMENTS 5,723,112 * 3/1998 Bowser ............................. 424/70.13

FOREIGN PATENT DOCUMENTS

| 0074819 | 3/1983 | (EP) . | |
|---|---|---|---|
| 0285389 | 10/1988 | (EP) . | |
| 0497163 | 8/1992 | (EP) . | |
| 0552024 | 7/1993 | (EP) . | |
| 0552024 A2 * | 7/1993 | (EP) | ............................. A61K/7/06 |
| 2258165 | 8/1975 | (FR) . | |
| 1066207 | 10/1965 | (GB) . | |
| 2246363 | 1/1992 | (GB) . | |
| 96/41610 | 12/1996 | (WO) . | |

* cited by examiner

*Primary Examiner*—Russell Travers
*Assistant Examiner*—Shengjun Wang
(74) *Attorney, Agent, or Firm*—Matthew Boxer

(57) ABSTRACT

The invention provides a washing composition for washing a surface to deposit thereon a solid active agent, the washing composition comprising an emulsion of silicone droplets, the silicone droplets comprising:

(a) a continuous silicone phase, and;

(b) a dispersed phase of solid particulate active agent.

Preferably the solid active agent is a solid antimicrobial such as zinc pyridinethione.

3 Claims, No Drawings

WASHING COMPOSITION

This application claims foreign priority of United Kingdom 9725013.8, filed Nov. 26, 1997.

1. Field of the Invention

The present invention relates to washing compositions, more particularly to washing compositions for washing a surface to deposit thereon a solid active agent, such as particles of a solid antimicrobial substance. Such washing compositions include compositions for washing hair or skin, such as hair shampoos, conditioners, body shampoos, shower gels, facial washing compositions, bar soaps and bath foams. They may also include compositions for household cleaning, such as hard surface cleaners.

2. Background and Prior Art

Difficulties arise in achieving effective deposition of solid active agents onto a surface such as skin or hair when the solid active agent is delivered by means of incorporation into rinse-off compositions, typically hair and body shampoos, conditioners and the like. Frequently, such active agents are preferentially rinsed away from the intended site of deposition, rather than being deposited thereat.

U.S. Pat. No. 5,037,818 describes that the presence of certain cationic polymers in aqueous washing compositions can enhance the deposition of water-insoluble particles such as solid antimicrobials.

There remains the problem, however, that the typical, preferred types of antimicrobial (such as sulphur, selenium disulphide and heavy metal salts of pyridinethione) are relatively dense materials and have a tendency to settle out on storage, from compositions into which they are incorporated. Therefore, in order for compositions containing these types of active agent to be aesthetically acceptable in the package and to provide a consistent, effective level of performance, without requiring vigorous shaking of the package in which they are contained, it is conventional practice to suspend them in the composition with a suspending agent. Examples of commonly used suspending agents include crystalline suspending agents (such as ethylene glycol distearate), inorganic structurants (such as swelling clays) and hydrophilic polymeric thickening agents (such as carbomers). Although these materials are effective for suspending particulate matter, they can adversely affect lathering performance, impart an undesirable cloudy appearance to the composition, and, in particular, mitigate against effective deposition of the active agent on the desired site, thereby reducing performance.

The present invention seeks to solve the above problems and to facilitate and/or enhance deposition of solid active agents, such as particulate antimicrobials, from washing compositions, particularly rinse-off compositions.

EP 0 552 024 describes a rinse-off cleaning composition including an emulsion comprising an internal oil phase of a silicone-type oil, in which the internal phase contains a surfactant soluble cosmetic agent, preferably dissolved therein. Phenylsilicones are particularly preferred silicone-type oils. Other alkyl-silicones are said to be less preferred owing to their inability to dissolve the hydrophobic materials which are the preferred cosmetic agents. The compositions are said to be particularly useful for enhancing deposition of surfactant soluble sunscreen materials from cleansing compositions such as shampoos.

We have now surprisingly found that solid active agents, such as particulate antimicrobials, can be successfully incorporated as a dispersed phase into the silicone phase of a silicone emulsion. Incorporation of the solid active agent into the silicone phase in this way enhances deposition and delivery of the solid active agent from a rinse-off washing composition, particularly in conjunction with a cationic polymer. Careful control of the silicone particle size may also, advantageously, enhance targeting of the active agent to the hair follicle.

SUMMARY OF THE INVENTION

In a first aspect, the present invention provides a washing composition for washing a surface to deposit thereon a solid active agent, the washing composition comprising an emulsion of silicone droplets, the silicone droplets comprising:

(a) a continuous silicone phase, and;

(b) a dispersed phase of solid particulate active agent.

In a second aspect, the invention provides a method of making an emulsion of silicone droplets comprising:

(a) a continuous silicone phase, and;

(b) a dispersed phase of solid particulate active agent, for incorporation into a washing composition, the method comprising the steps of:

(a) dispersing the solid active agent into silicone fluid, and (b) emulsifying the dispersion so obtained, thereby forming an emulsion of silicone droplets comprising:

(a) a continuous silicone phase, and;

(b) a dispersed phase of solid particulate active agent.

DETAILED DESCRIPTION AND PREFERRED EMBODIMENTS

The Emulsion

Washing compositions in accordance with this invention comprise an emulsion of silicone droplets, the silicone droplets comprising a continuous silicone phase, and a dispersed phase of solid particulate active agent.

The emulsion itself has a continuous phase (in which the silicone droplets are emulsified), which comprises one or more surfactants, at least as emulsifying agents for the silicone droplets, which may be present in an amount of from 0.1 to 50%, preferably 0.5 to 30%, typically 1 to 10% by weight of the emulsion.

Suitable emulsifiers are well known in the art and include anionic and nonionic emulsifiers. Examples of anionic emulsifiers are alkylarylsulphonates, e.g., sodium dodecylbenzene sulphonate, alkyl sulphates e.g., sodium, lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of nonionic emulsifiers are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

The continuous phase of the emulsion may, and preferably does, comprise water, preferably in an amount of from 0.1 to 70% by weight, typically 0.5 to 50% by weight of the emulsion.

Silicone Phase

Suitable silicones for the silicone phase are non-volatile silicone fluids, which may be one or more polyalkyl siloxanes, one or more polyalkylaryl siloxanes, or mixtures thereof. The silicone is present in an emulsified form, as dispersed droplets.

Suitable polyalkyl siloxanes include polydimethyl siloxanes which have the CTFA designation dimethicone, having a viscosity of from 5 to 1,000,000 centistokes at 25° C. These siloxanes are available commercially from the General Electric Company as the Viscasil series and from Dow Corning as the DC 200 series. The viscosity can be measured by means of a glass capillary viscometer as set out further in Dow Corning Corporate Test Method CTM004 Jul. 20, 1970.

Also suitable is polydiethyl siloxane.

Also suitable are silicone gums, such as those described in U.S. Pat. No. 4,152,416 (Spitzer), and on General Electric Silicone Rubber product Data Sheet SE 30, SE 33, SE 54 and SE 76. "Silicone gum" denotes polydiorganosiloxanes having a molecular weight of from 200,000 to 1,000,000 and specific examples include polydimethyl siloxane polymers, polydimethyl siloxane/diphenyl/methylvinylsiloxane copolymers, polydimethylsiloxane/methylvinylsiloxane copolymers and mixtures thereof.

Aminofunctional silicones which have the CTFA designation amodimethicone, are also suitable for use in the compositions of the invention, as are polydimethyl siloxanes having hydroxyl end groups (which have the CTFA designation dimethiconol).

The optimum viscosity for the silicone phase will depend on the physical properties of the solid active agent to be dispersed therein. In cases where the solid active agent is an antimicrobial such as a heavy metal (typically zinc) pyridinethione, it is generally advisable that the viscosity of the silicone phase is at least 10,000, preferably at least 50,000 centistokes, e.g 60,000 centistokes. We have found that this facilitates adequate retention of the dispersed phase of solid active agent within the droplets of the continuous silicone phase. If the viscosity of the continuous silicone phase is too low, then the dispersed particles of, e.g. zinc pyridinethione may tend to migrate towards the exterior surfaces of the droplets of silicone in which they are contained. If the viscosity is too high, then the washing composition may become difficult to process.

The average particle size of the silicone droplets in washing compositions according to this invention is suitably from 1 to 100 microns, preferably from 2 to 30 microns, more preferably 3 to 10 microns. A silicone particle size of from 3 to 10 microns is particularly preferred when the composition is intended for application to hair, since this size is believed to give optimum targeting of the silicone particles to the hair follicle, thereby optimising targeting of the solid active agent, e.g. an antimicrobial, to the hair follicle. Particle size may be measured by means of a laser light scattering technique, using a 2600D Particle Sizer from Malvern Instruments.

Washing compositions of the invention generally contain from 0.01 to 10%, preferably from 0.5 to 5% by weight based on the total washing composition, of silicone (the silicone per se and not the emulsion of silicone droplets). Particularly where the washing composition is a rinse-off cleansing shampoo composition for the hair or the body, if less than 0.01% by weight is present in the composition, little conditioning benefit will be attributable to the silicone, and if more than 10% by weight is present, the skin and/or hair may appear or feel greasy.

Solid Particulate Active Agent Phase

The nature of the solid particulate active agent employed in washing compositions of the invention is not critical and a wide variety of materials can be deposited onto various substrates from washing compositions in accordance with the invention. Materials which it is of practical benefit to deposit on substrates are mentioned in U.S. Pat. No. 3,489,686 and these can also be employed in the washing compositions of this invention. These include substances having an average particle diameter of from about 0.2 to about 50 microns, preferably from about 0.4 to about 10microns, and they may be anti-microbial agents, sunscreens, fabric brighteners, and various substances that create a favourable skin feel after washing. One class of solid active agent that is of special interest are the heavy metal salts, of pyridinethione, especially zinc pyridinethione.

Where the solid active agent is an antimicrobial agent, such as zinc pyridinethione, this may be suitably be employed in the washing composition in an amount of from 0.001% to about 1% by weight of the total composition.

Other suitable solid active agents include other antimicrobials such as climbazole, piroctone olamine, selenium sulphide and ketoconazole, pigment particles such as solid dyes or colorants suitable for application to hair and metal colloids.

Formulations

It is most preferred that the emulsion is formulated with additional components to form the final washing composition of the invention. Preferably, the emulsion constitutes from 1 to 100% by weight, typically from 1 to 70%, preferably from 5 to 60% by weight of the total washing composition.

Additional components which may be formulated with the emulsion into the final composition include surfactants, conditioning agents, polyols, thickening agents, deposition aids, pearlescers, buffers, as well as other optional adjunct materials such as foam boosters, perfumes, dyes, colouring agents, preservatives, proteins, polymers, moisturising agents, natural skin and hair nutrients (such as amino acids), hair fibre benefit agents (such as ceramides and lipids), fruit and herb extracts.

In preferred embodiments, the washing composition of the invention may,take the form of a rinse-off cleansing shampoo composition for the hair or the body, comprising one or more surfactants.

Further surfactants may be present as an additional ingredient if sufficient for cleansing purposes is not provided as the emulsifier for the emulsion of silicone droplets containing the dispersed solid active agent. Such further surfactants are typically selected from anionic, nonionic, zwitterionic and amphoteric surfactants or mixtures thereof.

In particularly preferred embodiments the washing composition of the invention may take the form of a rinse-off cleansing shampoo composition for the hair or the body, as described above, and in which the solid active agent is an antimicrobial agent, especially zinc pyridinethione or zirconium pyridinethione.

Surfactant

Suitable anionic surfactants for rinse-off cleansing shampoo compositions of the invention include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in shampoo compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di- ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamphopropionate.

The total amount of surfactant (including that used as emulsifier for the silicone droplets) in shampoo compositions of the invention is generally from 0.1 to 50% by weight, preferably from 5 to 30%, more preferably from 10% to 25% by weight of the total shampoo composition.

Deposition Polymer

A particularly preferred further component in shampoo compositions of the invention is a deposition polymer. This further enhances deposition of the silicone particles, and therefore the solid active agent contained therein, from the composition. This improves performance of the composition, and also cost-effectiveness, since enhanced deposition means that less of the solid active agent needs to be incorporated into the composition.

The deposition polymer may be a homopolymer or be formed from two or more types of monomers. The molecular weight of the polymer will generally be between 5,000 and 10,000,000, typically at least 10,000 and preferably in the range 10,0000 to about 2,000,000. The polymers will have cationic nitrogen containing groups such as quaternary ammonium or protonated amino groups, or a mixture thereof.

The cationic charge density is suitably at least 0.1 meq/g, preferably above 0.8 or higher. The cationic charge density should not exceed 3 meq/g. It is preferably less than 2 meq/g. The charge density can be measured using the Kjeldahl method and should be within the above limits at the desired pH of use, which will in general be from about 3 to 9 and preferably between 4 and 8.

The cationic nitrogen-containing group will generally be present as a substituent on a fraction of the total monomer units of the cationic deposition polymer. Thus when the polymer is not a homopolymer it can contain spacer non-cationic monomer units. Such polymers are described in the CTFA Cosmetic Ingredient Directory, 3rd edition.

Suitable cationic deposition polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$–$C_3$ alkyls, more preferably $C_1$ and $C_2$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic deposition polymers can comprise mixtures of monomer units derived from amine- and/or quaternary ammonium-substituted monomer and/or compatible spacer monomers.

Suitable cationic deposition polymers include, for example: copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA". as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gaf Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in our copending UK Application No. 9403156.4 (WO95/22311).

Other cationic deposition polymers that can be used include polysaccharide polymers, such as cationic cellulose derivatives and cationic starch derivatives.

Cationic polysaccharide polymer materials suitable for use in compositions of the invention include those of the formula:

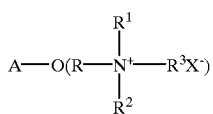

wherein: A is an anhydroglucose residual group, such as starch or cellulose anhydroglucose residual, R is an alkylene, oxyalkylene, polyoxyalkylene, or hydroxyalkylene group, or combination thereof, $R^1$, $R^2$ and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion, as previously described.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic deposition polymers that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g. as described in U.S. Pat. No. 3,962,418), and copolymers of etherified cellulose and starch (e.g., as described in U.S. Pat. No. 3,958,581.

Preferably the cationic deposition polymer is selected from the group comprising cationic polyacrylamides, hydroxyalkyl cellulose ethers and cationic guar derivatives. Particularly preferred are Jaguar C13S with a cationic charge density of 0.8 meq/g. Jaguar C13S is guar hydroxypropyltriamonium chloride. Other particularly suitable materials include Jaguar C15, Jaguar C17 and Jaguar C16 and Jaguar C162, A preferred cellulose ether is Polymer JR400.

The particular level appropriate in shampoo compositions of the present invention is dependent on the particular surfactant system employed. Generally, the level can vary from 0.01 to 10%, preferably 0.02 to 5%, typically 0.05 to 1% by weight of the total shampoo composition.

Shampoo compositions of this invention may optionally further comprise from 0.1 to 5% of a silicone suspending agent. Examples are polyacrylic acids, cross linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and Polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark.

Suitable cross linked polymers of acrylic acid and acrylate esters are Pemulen TR1 or Pemulen TR2. A suitable heteropolysaccharide gum is xanthan gum, for example that available as Kelzan mu.

Conditioning Agent

Shampoo compositions of the invention may optionally further comprise one or more conditioning agents, in addition to the silicone droplets already present, which, advantageously, impart a conditioning benefit.

Suitable further conditioning agents include cationic surfactants, (such as quaternary ammonium halides), Quaternium-5, Quaternium-31, Quaternium-18, protein hydrolysates, quaternised protein hydrolysates, perfluoropolyether materials, fatty acids, fatty alcohols and mixtures thereof.

Such further conditioning agents, if present, are generally present in washing compositions of the invention in a total amount of from 0.1 to 10% by weight, preferably in an amount of from 0.2 to 5% by weight of the total washing composition.

Preparation and final form of the washing compositions

The washing compositions in accordance with the invention may be prepared by first dispersing the solid active agent into silicone fluid, and then emulsifying the dispersion so obtained, thereby forming an emulsion of silicone droplets comprising a continuous silicone phase, and a dispersed phase of the solid particulate active agent.

Optional ingredients as decribed above may be added at the emulsification stage, the emulsification being effected by high speed stirring/mixing in accordance with conventional techniques.

If the emulsion is to be formulated with other ingredients into the final washing composition, this is achieved by simple mixing, as is well known in the art.

In cases where the solid active agent is an antimicrobial such as a heavy metal (typically zinc) pyridinethione, it is generally advisable that the viscosity of the silicone phase is at least 10,000, preferably at least 50,000 centistokes, e.g 60,000 centistokes, for reasons described above (see heading "Silicone Phase").

We have also found in such cases that it is advantageous if, in a first stage, the solid active agent is pre-wetted with a low viscosity silicone. By "low viscosity silicone" is meant a silicone fluid (typically a polyalkyl siloxane or a polyalkylaryl siloxane), with a viscosity ranging from about 5 to 500 centistokes, preferably from about 5 to 200 centistokes. Good results have been obtained for the solid active agent zinc pyridinethione when pre-wetted with dimethicone fluid of viscosity 100 centistokes (available from Dow Corning as the "DC200"series).

However this pre-wetting step may not always be necessary if an appropriate mixing regime is employed to facilitate incorporation of the soild active agent.

Use of the washing composition

The compositions of the invention may take any suitable form appropriate to the solid active agent which they contain and are intended to deposit. By suitable selection of essential and non-essential ingredients and relative amounts thereof, the washing compositions of the invention may be in the form of, for example, hair shampoos and other rinse-off hair treatment compositions, body shampoos, shower gels, facial washing compositions, bar soaps, bath foams and the like. Preferred compositions in the form of body or hair shampoos may be applied to the skin or hair, as appropriate, and worked to create a lather. The lather may be retained at the applied site for a short time, e.g. one or several minutes, before rinsing, or may be immediately rinsed. The procedure may be repeated if desired.

Retention of the lather at the site of application and repetition of the application regime may be of additional benefit in enhancing even further the amount or rate of deposition of the solid active agent on the skin or hair surface, and/or its delivery to the hair follicle.

Other Applications

In general, however, a washing composition according to this invention may also be one suitable for the washing of fabrics, where the solid active agent comprises particles of a fabric conditioning or treating agent, for example an acrylic latex; or for the washing of hard surfaces where the solid active agent may comprise a germicide, as in, for example, compositions for the cleaning of toilets. Alternatively, the solid active agent may comprise a polymer latex designed to leave a polymer film on a cleaned surface, for example to provide a glossy appearance to the surface. The washing composition of the invention may also find application in the field of oral hygiene where the deposition during use of an oral treatment composition of particles comprising an active compound for the care of the oral cavity, may be beneficial.

The invention is further illustrated by the following non-limiting Examples.

EXAMPLES

Example 1

Preparation of an emulsion of silicone droplets containing the solid antimicrobial active Zinc Pyrithione in the silicone phase 5 g of Zinc Pyrithione (Aldrich, dry powder) was mixed with 15 g of silicone oil (100 Cs, Dow Corning) to form a creamy viscous liquid. To this mixture, a further 30 g of high viscosity silicone oil (60,000 Cs, Dow Corning) was added and the mixture stirred thoroughly.

150 g of SLES-2EO (26%) was stirred, and 11 g of the Zinc Pyrithione/silicone oil mixture prepared as described above was added. The mixture was stirred until a homogeneous dispersion was formed. To this was added 11 g of a 10% Carbopol gel and the mixture again stirred until homogeneous.

Observation under optical microscopy showed that the product comprised an emulsion of silicone oil droplets, with Zinc Pyrithione predominantly encased within the silicone oil droplets.

Example 2

Preparation of a shampoo composition

The emulsion of Example 1 was formulated into a shampoo composition by mixing with a solution of SLES-2EO, JAGUAR C13S and formalin to give a shampoo having the composition shown in the Table below, in which all amounts are expressed in % by weight of the total shampoo composition.

TABLE

| Ingredient | % by weight |
| --- | --- |
| Zinc Pyrithione | 0.55 |
| silicone oil (100 Cs) | 1.65 |
| silicone oil (60,000 Cs) | 3.30 |
| SLES-2EO. | 16.00 |
| JAGUAR C13S | 0.30 |
| Carbopol | 0.55 |
| Formalin | 0.10 |
| Water | to 100 |

What is claimed:

1. An emulsion of silicone droplets comprising:

(a) a continuous silicone phase; and (b) a dispersed phase of particulate zinc pyridinethione active agent for incorporation into a washing composition, and made by the steps of:

(1) pre-wetting the solid particulate zinc pyridinethione with a low viscosity silicone fluid, (2) dispersing the particulate zinc pyridinethione into a higher viscosity silicone fluid, (3) emulsifying the dispersion so obtained, thereby forming an emulsion of silicone droplets.

2. A method of making an emulsion of silicone droplets comprising:

(a) a continuous silicone phase; and (b) a dispersed phase of solid particulate active agent, for incorporation into a washing composition, the method comprising the steps of:

(1) dispersing the solid particulate active agent into silicone fluid; and (2) emulsifying the dispersion so obtained, thereby forming an emulsion of silicone droplets comprising:

(i) a continuous silicone phase; and (ii) a dispersed phase of solid particulate active agent;

wherein said solid particulate active agent is zinc pyridinethione and wherein said continuous silicone phase has a viscosity of at least 10,000 centistokes, and wherein in a first stage, the solid active particulate agent is pre-wetted with a low viscosity silicone, of viscosity ranging from about 5 to about 500 centistokes.

3. A method in accordance with claim 2, wherein the viscosity of said continuous silicone phase is at least 50,000 centistokes and wherein said low viscosity silicone has a viscosity ranging from about 5 to about 200 centistokes.

* * * * *